United States Patent [19]

Weaver

[11] Patent Number: 6,031,075
[45] Date of Patent: *Feb. 29, 2000

[54] MATURE ALVEOLAR SP-B AND A PROCESS FOR PRODUCING THE SAME

[75] Inventor: Timothy E. Weaver, Loveland, Ohio

[73] Assignee: Children's Hospital Medical Center, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/596,684

[22] Filed: Feb. 5, 1996

[51] Int. Cl.$^7$ ............................ C07K 14/785; C07K 1/22
[52] U.S. Cl. ...................... 530/350; 530/324; 530/344; 530/415; 530/811; 514/12
[58] Field of Search ..................... 530/324, 350, 530/344, 811, 415; 514/12

[56] References Cited

U.S. PATENT DOCUMENTS

| | | | |
|---|---|---|---|
| 4,933,280 | 6/1990 | Schilling, Jr. et al. | 435/69.1 |
| 4,977,248 | 12/1990 | Creighton | 530/412 |
| 5,008,377 | 4/1991 | Patroni et al. | 530/416 |
| 5,164,369 | 11/1992 | Cochrane et al. | 514/12 |
| 5,258,496 | 11/1993 | Benson et al. | 530/350 |
| 5,403,915 | 4/1995 | Benson et al. | 530/350 |
| 5,430,020 | 7/1995 | Schilling, Jr. et al. | 514/12 |

FOREIGN PATENT DOCUMENTS

| | | |
|---|---|---|
| WO 8805820 | 8/1988 | WIPO . |
| 90 01 540 | 2/1990 | WIPO . |

OTHER PUBLICATIONS

Pilot–Matias et al., "Structure and Organization of the Gene Encoding Human Pulmonary Surfactant Proteolipid SP–B," (1989), DNA 8:75–86.

Yao et al., "Expression of Mature Pulmonary Surfactant–associated Protein B (SP–B) in *Escherichia coli* Using Truncated Human SP–B cDNAs," (1990), Biochemistry and Cell Biology 68:559–566.

Johansson et al., "Human Surfactant Polypeptide SP–B: Disulfide bridges, C–terminal end, and peptide analysis of the airway form," (1992), FEBS Letters 301:165–167.

Weaver et al., "Processing of Surfactant Protein B Proprotein by a Cathepsin D–like Protease," (1992) American Journal of Physiology L95–L103.

T. E. Weaver and J. A. Whitsett, "Processing of Hydrophobic Pulmonary Surfactant Protein B in Rat Type II Cells," (1989) American Journal of Physiology L100–L108.

Kuhelj et al., "The Preparation of Catalytically Active Human Cathepsin B from its Precursor Expressed in *Escherichia coli* in the Form of Inclusion Bodies," (1995) European Journal of Biochemistry 229:533–539.

A. Leuthardt and J. L. Roesel, "Cloning, Expression and Purification of a Recombinant Poly–Histidine–Linked HIV–1 Protease," (1993) FEBS Letters 326:275–280.

Sinha et al., "Ligand Binding Assays with Recombinant Proteins Refolded on an Affinity Matrix," (1994) Biotechniques 17:509–514.

Suttnar et al., "Procedure for Refolding and Purification of Recombinant Proteins from *Escherichia coli* Inclusion Bodies Using a Strong Anion Exchanger," (1994) Journal of Chromatography B 656:123–126.

Holzinger A; Phillips K S; Weaver T E. Single–step purification/solubilization of recombinant proteins: application to surfactant protein B. Biotechniques, (May 1996) 20 (5) 804–806.

Hochuli E; Bannwarth W; Dobeli H; Gentz R; Stuber D. Genetic approach to facilitate purification of recombinant proteins with a novel metal chelate adsorbent. Bio–Technology (N Y) 6 (11). Nov. 1988. 1321–1325.

Porath, J. Modern Methods in Protein Chemistry, eds. Tschesche, H. (de Gruyter, Berlin), vol. 2, pp. 85–95, (1985).

Hemdan, S. E. Proc. Natl. Acad. Sci. U.S.A. vol. 86, pp. 1811–1815, 1989.

Rudolf, R. "Renaturation of recombinant, disulfide–bonded proteins from inclusion bodies", In, Modern Methods in Protein and Nucleic Acid Research, 1990, pp. 149–171.

Glasser et al. cDNA and deduced amino acid sequence of human pulmonary surfactant–associated proteolipid SPL-(Phe). Proc. Natl. Acad. Sci. U.S.A. (Jun. 1987) 84:4007–4011.

*Primary Examiner*—Elizabeth Kemmerer
*Assistant Examiner*—David S. Romeo
*Attorney, Agent, or Firm*—Wood, Herron & Evans, L.L.P.

[57] ABSTRACT

Mature alveolar surfactant protein B and a process for producing the same is disclosed. The process includes the use of a fusion protein of SP-B having a propeptide only at its amino terminus. A propeptide at its carboxyl terminus is not necessary, and thus not included in the fusion protein, to produce the mature SP-B of this process. Cleavage of the amino-terminus propeptide results in the production of mature SP-B.

17 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1146 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 1...1143
      (D) OTHER INFORMATION:
      (A) NAME/KEY: Signal Sequence
      (B) LOCATION: 1...601
      (D) OTHER INFORMATION:

(xi) SEQUENCE DESCRIPTION: SEQ ID NO:1:

```
ATG GCT GAG TCA CAC CTG CTG CAG TGG CTG CTG CTG CTG CCC ACG           48
Met Ala Glu Ser His Leu Leu Gln Trp Leu Leu Leu Leu Pro Thr
-200             -195             -190             -185

CTC TGT GGC CCA GGC ACT GCT GCC TGG ACC ACC TCA TCC TTG GCC TGT       96
Leu Cys Gly Pro Gly Thr Ala Ala Trp Thr Thr Ser Ser Leu Ala Cys
            -180             -175             -170

GCC CAG GGC CCT GAG TTC TGG TGC CAA AGC CTG GAG CAA GCA TTG CAG      144
Ala Gln Gly Pro Glu Phe Trp Cys Gln Ser Leu Glu Gln Ala Leu Gln
            -165             -160             -155

TGC AGA GCC CTA GGG CAT TGC CTA CAG GAA GTC TGG GGA CAT GTG GGA      192
Cys Arg Ala Leu Gly His Cys Leu Gln Glu Val Trp Gly His Val Gly
            -150             -145             -140

GCC GAT GAC CTA TGC CAA GAG TGT GAG GAC ATC GTC CAC ATC CTT AAC      240
Ala Asp Asp Leu Cys Gln Glu Cys Glu Asp Ile Val His Ile Leu Asn
            -135             -130             -125

AAG ATG GCC AAG GAG GCC ATT TTC CAG GAC ACG ATG AGG AAG TTC CTG      288
Lys Met Ala Lys Glu Ala Ile Phe Gln Asp Thr Met Arg Lys Phe Leu
-120             -115             -110             -105

GAG CAG GAG TGC AAC GTC CTC CCC TTG AAG CTG CTC ATG CCC CAG TGC      336
Glu Gln Glu Cys Asn Val Leu Pro Leu Lys Leu Leu Met Pro Gln Cys
            -100             -95              -90

AAC CAA GTG CTT GAC GAC TAC TTC CCC CTG GTC ATC GAC TAC TTC CAG      384
Asn Gln Val Leu Asp Asp Tyr Phe Pro Leu Val Ile Asp Tyr Phe Gln
            -85              -80              -75

AAC CAG ACT GAC TCA AAC GGC ATC TGT ATG CAC CTG GGC CTG TGC AAA      432
Asn Gln Thr Asp Ser Asn Gly Ile Cys Met His Leu Gly Leu Cys Lys
            -70              -65              -60

TCC CGG CAG CCA GAG CCA GAG CAG GAG CCA GGG ATG TCA GAC CCC CTG      480
Ser Arg Gln Pro Glu Pro Glu Gln Glu Pro Gly Met Ser Asp Pro Leu
            -55              -50              -45
```

-continued

```
CCC AAA CCT CTG CGG GAC CCT CTG CCA GAC CCT CTG CTG GAC AAG CTC     528
Pro Lys Pro Leu Arg Asp Pro Leu Pro Asp Pro Leu Leu Asp Lys Leu
    -40             -35             -30             -25

GTC CTC CCT GTG CTG CCC GGG GCC CTC CAG GCG AGG CCT GGG CCT CAC     576
Val Leu Pro Val Leu Pro Gly Ala Leu Gln Ala Arg Pro Gly Pro His
            -20             -15             -10

ACA CAG GAT CTC TCC GAG CAG CAA TTC CCC ATT CCT CTC CCC TAT TGC     624
Thr Gln Asp Leu Ser Glu Gln Gln Phe Pro Ile Pro Leu Pro Tyr Cys
                -5               1               5

TGG CTC TGC AGG GCT CTG ATC AAG CGG ATC CAA GCC ATG ATT CCC AAG     672
Trp Leu Cys Arg Ala Leu Ile Lys Arg Ile Gln Ala Met Ile Pro Lys
        10              15              20

GGT GCG CTA GCT GTG GCA GTG GCC CAG GTG TGC CGC GTG GTA CCT CTG     720
Gly Ala Leu Ala Val Ala Val Ala Gln Val Cys Arg Val Val Pro Leu
    25              30              35              40

GTG GCG GGC GGC ATC TGC CAG TGC CTG GCT GAG CGC TAC TCC GTC ATC     768
Val Ala Gly Gly Ile Cys Gln Cys Leu Ala Glu Arg Tyr Ser Val Ile
                45              50              55

CTG CTC GAC ACG CTG CTG GGC CGC ATG CTG CCC CAG CTG GTC TGC CGC     816
Leu Leu Asp Thr Leu Leu Gly Arg Met Leu Pro Gln Leu Val Cys Arg
            60              65              70

CTC GTC CTC CGG TGC TCC ATG GAT GAC AGC GCT GGC CCA AGG TCG CCG     864
Leu Val Leu Arg Cys Ser Met Asp Asp Ser Ala Gly Pro Arg Ser Pro
        75              80              85

ACA GGA GAA TGG CTG CCG CGA GAC TCT GAG TGC CAC CTC TGC ATG TCC     912
Thr Gly Glu Trp Leu Pro Arg Asp Ser Glu Cys His Leu Cys Met Ser
    90              95              100

GTG ACC ACC CAG GCC GGG AAC AGC AGC GAG CAG GCC ATA CCA CAG GCA     960
Val Thr Thr Gln Ala Gly Asn Ser Ser Glu Gln Ala Ile Pro Gln Ala
105             110             115             120

ATG CTC CAG GCC TGT GTT GGC TCC TGG CTG GAC AGG GAA AAG TGC AAG    1008
Met Leu Gln Ala Cys Val Gly Ser Trp Leu Asp Arg Glu Lys Cys Lys
        125             130             135

CAA TTT GTG GAG CAG CAC ACG CCC CAG CTG CTG ACC CTG GTG CCC AGG    1056
Gln Phe Val Glu Gln His Thr Pro Gln Leu Leu Thr Leu Val Pro Arg
            140             145             150

GGC TGG GAT GCC CAC ACC ACC TGC CAG GCC CTC GGG GTG TGT GGG ACC    1104
Gly Trp Asp Ala His Thr Thr Cys Gln Ala Leu Gly Val Cys Gly Thr
        155             160             165

ATG TCC AGC CCT CTC CAG TGT ATC CAC AGC CCC GAC CTT TGA            1146
Met Ser Ser Pro Leu Gln Cys Ile His Ser Pro Asp Leu
    170             175             180

(2) INFORMATION FOR SEQ ID NO:2:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...237
        (D) OTHER INFORMATION:
        (A) NAME/KEY: mat_peptide
        (B) LOCATION: 1...79
        (D) OTHER INFORMATION:

(xi) SEQUENCE DESCRIPTION: SEQ ID NO:2:

TTC CCC ATT CCT CTC CCC TAT TGC TGG CTC TGC AGG GCT CTG ATC AAG      48
Phe Pro Ile Pro Leu Pro Tyr Cys Trp Leu Cys Arg Ala Leu Ile Lys
1               5               10              15
```

```
CGG ATC CAA GCC ATG ATT CCC AAG GGT GCG CTA GCT GTG GCA GTG GCC    96
Arg Ile Gln Ala Met Ile Pro Lys Gly Ala Leu Ala Val Ala Val Ala
             20                  25                  30

CAG GTG TGC CGC GTG GTA CCT CTG GTG GCG GGC GGC ATC TGC CAG TGC   144
Gln Val Cys Arg Val Val Pro Leu Val Ala Gly Gly Ile Cys Gln Cys
         35                  40                  45

CTG GCT GAG CGC TAC TCC GTC ATC CTG CTC GAC ACG CTG CTG GGC CGC   192
Leu Ala Glu Arg Tyr Ser Val Ile Leu Leu Asp Thr Leu Leu Gly Arg
 50                  55                  60

ATG CTG CCC CAG CTG GTC TGC CGC CTC GTC CTC CGG TGC TCC ATG       237
Met Leu Pro Gln Leu Val Cys Arg Leu Val Leu Arg Cys Ser Met
 65                  70                  75
```

(2) INFORMATION FOR SEQ ID NO:3:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...768
        (D) OTHER INFORMATION:
        (A) NAME/KEY: Signal Sequence
        (B) LOCATION: 1...532
        (D) OTHER INFORMATION:

(xi) SEQUENCE DESCRIPTION: SEQ ID NO:3:

```
GCC TGG ACC ACC TCA TCC TTG GCC TGT GCC CAG GGC CCT GAG TTC TGG    48
Ala Trp Thr Thr Ser Ser Leu Ala Cys Ala Gln Gly Pro Glu Phe Trp
         -175                -170                -165

TGC CAA AGC CTG GAG CAA GCA TTG CAG TGC AGA GCC CTA GGG CAT TGC    96
Cys Gln Ser Leu Glu Gln Ala Leu Gln Cys Arg Ala Leu Gly His Cys
    -160                -155                -150

CTA CAG GAA GTC TGG GGA CAT GTG GGA GCC GAT GAC CTA TGC CAA GAG   144
Leu Gln Glu Val Trp Gly His Val Gly Ala Asp Asp Leu Cys Gln Glu
-145                -140                -135                -130

TGT GAG GAC ATC GTC CAC ATC CTT AAC AAG ATG GCC AAG GAG GCC ATT   192
Cys Glu Asp Ile Val His Ile Leu Asn Lys Met Ala Lys Glu Ala Ile
            -125                -120                -115

TTC CAG GAC ACG ATG AGG AAG TTC CTG GAG CAG GAG TGC AAC GTC CTC   240
Phe Gln Asp Thr Met Arg Lys Phe Leu Glu Gln Glu Cys Asn Val Leu
        -110                -105                -100

CCC TTG AAG CTG CTC ATG CCC CAG TGC AAC CAA GTG CTT GAC GAC TAC   288
Pro Leu Lys Leu Leu Met Pro Gln Cys Asn Gln Val Leu Asp Asp Tyr
    -95                 -90                 -85

TTC CCC CTG GTC ATC GAC TAC TTC CAG AAC CAG ACT GAC TCA AAC GGC   336
Phe Pro Leu Val Ile Asp Tyr Phe Gln Asn Gln Thr Asp Ser Asn Gly
-80                 -75                  -70

ATC TGT ATG CAC CTG GGC CTG TGC AAA TCC CGG CAG CCA GAG CCA GAG   384
Ile Cys Met His Leu Gly Leu Cys Lys Ser Arg Gln Pro Glu Pro Glu
-65                 -60                  -55                 -50

CAG GAG CCA GGG ATG TCA GAC CCC CTG CCC AAA CCT CTG CGG GAC CCT   432
Gln Glu Pro Gly Met Ser Asp Pro Leu Pro Lys Pro Leu Arg Asp Pro
                -45                 -40                 -35

CTG CCA GAC CCT CTG CTG GAC AAG CTC GTC CTC CCT GTG CTG CCC GGG   480
Leu Pro Asp Pro Leu Leu Asp Lys Leu Val Leu Pro Val Leu Pro Gly
            -30                 -25                 -20

GCC CTC CAG GCG AGG CCT GGG CCT CAC ACA CAG GAT CTC TCC GAG CAG   528
Ala Leu Gln Ala Arg Pro Gly Pro His Thr Gln Asp Leu Ser Glu Gln
        -15                 -10                 -5
```

```
CAA TTC CCC ATT CCT CTC CCC TAT TGC TGG CTC TGC AGG GCT CTG ATC        576
Gln Phe Pro Ile Pro Leu Pro Tyr Cys Trp Leu Cys Arg Ala Leu Ile
 1               5                  10                  15

AAG CGG ATC CAA GCC ATG ATT CCC AAG GGT GCG CTA GCT GTG GCA GTG        624
Lys Arg Ile Gln Ala Met Ile Pro Lys Gly Ala Leu Ala Val Ala Val
                 20                  25                  30

GCC CAG GTG TGC CGC GTG GTA CCT CTG GTG GCG GGC GGC ATC TGC CAG        672
Ala Gln Val Cys Arg Val Val Pro Leu Val Ala Gly Gly Ile Cys Gln
                 35                  40                  45

TGC CTG GCT GAG CGC TAC TCC GTC ATC CTG CTC GAC ACG CTG CTG GGC        720
Cys Leu Ala Glu Arg Tyr Ser Val Ile Leu Leu Asp Thr Leu Leu Gly
         50                  55                  60

CGC ATG CTG CCC CAG CTG GTC TGC CGC CTC GTC CTC CGG TGC TCC ATG        768
Arg Met Leu Pro Gln Leu Val Cys Arg Leu Val Leu Arg Cys Ser Met
 65                  70                  75
```

(2) INFORMATION FOR SEQ ID NO:4:

(i) SEQUENCE CHARACTERISTICS:
        (A) LENGTH: 237 base pairs
        (B) TYPE: nucleic acid
        (C) STRANDEDNESS: unknown
        (D) TOPOLOGY: linear (ix) FEATURE:
        (A) NAME/KEY: Coding Sequence
        (B) LOCATION: 1...237
        (D) OTHER INFORMATION:
        (A) NAME/KEY: mat_peptide
        (B) LOCATION: 1...237
        (D) OTHER INFORMATION:

(xi) SEQUENCE DESCRIPTION: SEQ ID NO:4:

```
GGC CCC ATT CCT CTC CCC TAT TGC TGG CTC TGC AGG GCT CTG ATC AAG         48
Gly Pro Ile Pro Leu Pro Tyr Cys Trp Leu Cys Arg Ala Leu Ile Lys
 1               5                  10                  15

CGG ATC CAA GCC ATG ATT CCC AAG GGT GCG CTA GCT GTG GCA GTG GCC         96
Arg Ile Gln Ala Met Ile Pro Lys Gly Ala Leu Ala Val Ala Val Ala
                 20                  25                  30

CAG GTG TGC CGC GTG GTA CCT CTG GTG GCG GGC GGC ATC TGC CAG TGC        144
Gln Val Cys Arg Val Val Pro Leu Val Ala Gly Gly Ile Cys Gln Cys
             35                  40                  45

CTG GCT GAG CGC TAC TCC GTC ATC CTG CTC GAC ACG CTG CTG GGC CGC        192
Leu Ala Glu Arg Tyr Ser Val Ile Leu Leu Asp Thr Leu Leu Gly Arg
     50                  55                  60

ATG CTG CCC CAG CTG GTC TGC CGC CTC GTC CTC CGG TGC TCC ATG            237
Met Leu Pro Gln Leu Val Cys Arg Leu Val Leu Arg Cys Ser Met
 65                  70                  75
```

(2) INFORMATION FOR SEQ ID NO:5:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...768
        (D) OTHER INFORMATION:
        (A) NAME/KEY: Signal Sequence
        (B) LOCATION: 1...532
        (D) OTHER INFORMATION:

(xi) SEQUENCE DESCRIPTION: SEQ ID NO:5:

```
GCC TGG ACC ACC TCA TCC TTG GCC TGT GCC CAG GGC CCT GAG TTC TGG         48
```

```
Ala Trp Thr Thr Ser Ser Leu Ala Cys Ala Gln Gly Pro Glu Phe Trp
      -175             -170                 -165

TGC CAA AGC CTG GAG CAA GCA TTG CAG TGC AGA GCC CTA GGG CAT TGC        96
Cys Gln Ser Leu Glu Gln Ala Leu Gln Cys Arg Ala Leu Gly His Cys
        -160             -155             -150

CTA CAG GAA GTC TGG GGA CAT GTG GGA GCC GAT GAC CTA TGC CAA GAG       144
Leu Gln Glu Val Trp Gly His Val Gly Ala Asp Asp Leu Cys Gln Glu
-145             -140             -135             -130

TGT GAG GAC ATC GTC CAC ATC CTT AAC AAG ATG GCC AAG GAG GCC ATT       192
Cys Glu Asp Ile Val His Ile Leu Asn Lys Met Ala Lys Glu Ala Ile
            -125             -120             -115

TTC CAG GAC ACG ATG AGG AAG TTC CTG GAG CAG GAG TGC AAC GTC CTC       240
Phe Gln Asp Thr Met Arg Lys Phe Leu Glu Gln Glu Cys Asn Val Leu
            -110             -105             -100

CCC TTG AAG CTG CTC ATG CCC CAG TGC AAC CAA GTG CTT GAC GAC TAC       288
Pro Leu Lys Leu Leu Met Pro Gln Cys Asn Gln Val Leu Asp Asp Tyr
        -95             -90              -85

TTC CCC CTG GTC ATC GAC TAC TTC CAG AAC CAG ACT GAC TCA CAA GGC       336
Phe Pro Leu Val Ile Asp Tyr Phe Gln Asn Gln Thr Asp Ser Gln Gly
        -80             -75              -70

ATC TGT ATG CAC CTG GGC CTG TGC AAA TCC CGG CAG CCA GAG CCA GAG       384
Ile Cys Met His Leu Gly Leu Cys Lys Ser Arg Gln Pro Glu Pro Glu
-65             -60              -55              -50

CAG GAG CCA GGG ATG TCA GAC CCC CTG CCC AAA CCT CTG CGG GAC CCT       432
Gln Glu Pro Gly Met Ser Asp Pro Leu Pro Lys Pro Leu Arg Asp Pro
            -45              -40              -35

CTG CCA GAC CCT CTG CTG GAC AAG CTC GTC CTC CCT GTG CTG CCC GGG       480
Leu Pro Asp Pro Leu Leu Asp Lys Leu Val Leu Pro Val Leu Pro Gly
            -30              -25              -20

GCC CTC CAG GCG AGG CCT GGG CCT CAC ACA CAG GAT CTC TCC GAG CAG       528
Ala Leu Gln Ala Arg Pro Gly Pro His Thr Gln Asp Leu Ser Glu Gln
        -15              -10               -5

AAC GGC CCC ATT CCT CTC CCC TAT TGC TGG CTC TGC AGG GCT CTG ATC       576
Asn Gly Pro Ile Pro Leu Pro Tyr Cys Trp Leu Cys Arg Ala Leu Ile
  1               5                10               15

AAG CGG ATC CAA GCC ATG ATT CCC AAG GGT GCG CTA GCT GTG GCA GTG       624
Lys Arg Ile Gln Ala Met Ile Pro Lys Gly Ala Leu Ala Val Ala Val
              20               25               30

GCC CAG GTG TGC CGC GTG GTA CCT CTG GTG GCG GGC GGC ATC TGC CAG       672
Ala Gln Val Cys Arg Val Val Pro Leu Val Ala Gly Gly Ile Cys Gln
             35               40               45

TGC CTG GCT GAG CGC TAC TCC GTC ATC CTG CTC GAC ACG CTG CTG GGC       720
Cys Leu Ala Glu Arg Tyr Ser Val Ile Leu Leu Asp Thr Leu Leu Gly
             50               55               60

CGC ATG CTG CCC CAG CTG GTC TGC CGC CTC GTC CTC CGG TGC TCC ATG       768
Arg Met Leu Pro Gln Leu Val Cys Arg Leu Val Leu Arg Cys Ser Met
    65               70               75
```

(2) INFORMATION FOR SEQ ID NO:6:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: mat_peptide
        (B) LOCATION: 1...79

(D) OTHER INFORMATION:

(xi) SEQUENCE DESCRIPTION: SEQ ID NO:6:

```
Gly Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
                20                  25                  30

Gln Val Cys Arg Val Val Pro Leu Val Ala Gly Gly Ile Cys Gln Cys
            35                  40                  45

Leu Ala Glu Arg Tyr Ser Val Ile Leu Leu Asp Thr Leu Leu Gly Arg
        50                  55                  60

Met Leu Pro Gln Leu Val Cys Arg Leu Val Leu Arg Cys Ser Met
65                  70                  75
```

(2) INFORMATION FOR SEQ ID NO:7:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: protein (v) FRAGMENT TYPE: N-terminal (ix) FEATURE:
        (A) NAME/KEY: Signal Sequence
        (B) LOCATION: 1...178
        (D) OTHER INFORMATION:

(xi) SEQUENCE DESCRIPTION: SEQ ID NO:7:

```
Ala Trp Thr Thr Gly Ser Ser Leu Ala Cys Ala Gln Gly Pro Glu Phe
        -175                -170                -165

Trp Cys Gln Ser Leu Glu Gln Ala Leu Gln Cys Arg Ala Leu Gly His
        -160                -155                -150

Cys Leu Gln Glu Val Trp Gly His Val Gly Ala Asp Asp Leu Cys Gln
        -145                -140                -135

Glu Cys Glu Asp Ile Val His Ile Leu Asn Lys Met Ala Lys Glu Ala
-130                -125                -120                -115

Ile Phe Gln Asp Thr Met Arg Lys Phe Leu Glu Gln Glu Cys Asn Val
                -110                -105                -100

Leu Pro Leu Lys Leu Leu Met Pro Gln Cys Asn Gln Val Leu Asp Asp
                -95                 -90                 -85

Tyr Phe Pro Leu Val Ile Asp Tyr Phe Gln Asn Gln Thr Asp Ser Gln
            -80                 -75                 -70

Gly Ile Cys Met His Leu Gly Leu Cys Lys Ser Arg Gln Pro Glu Pro
        -65                 -60                 -55

Glu Gln Glu Pro Gly Met Ser Asp Pro Leu Pro Lys Pro Leu Arg Asp
-50                 -45                 -40                 -35

Pro Leu Pro Asp Pro Leu Leu Asp Lys Leu Val Leu Pro Val Leu Pro
                -30                 -25                 -20

Gly Ala Leu Gln Ala Arg Pro Gly Pro His Thr Gln Asp Leu Ser Glu
            -15                 -10                 -5

Gln Asn Gly Pro Ile Pro Leu Pro Tyr Cys Trp Leu Cys Arg Ala Leu
        1                   5                   10

Ile Lys Arg Ile Gln Ala Met Ile Pro Lys Gly Ala Leu Ala Val Ala
15                  20                  25                  30

Val Ala Gln Val Cys Arg Val Val Pro Leu Val Ala Gly Gly Ile Cys
```

```
                    35                  40                  45
Gln Cys Leu Ala Glu Arg Tyr Ser Val Ile Leu Leu Asp Thr Leu Leu
                50                  55                  60

Gly Arg Met Leu Pro Gln Leu Val Cys Arg Leu Val Leu Arg Cys Ser
            65                  70                  75
Met
```

MATURE ALVEOLAR SP-B AND A PROCESS FOR PRODUCING THE SAME

FIELD OF THE INVENTION

This invention relates generally to lung surfactant proteins, and more particularly to lung surfactant protein B and a process for producing the same.

BACKGROUND OF THE INVENTION

Pulmonary surfactant is a phospholipid-rich mixture which is secreted into the alveolar space by the type II epithelial cell. Formation of a surfactant film at the epithelial-air interface helps to maintain alveolar integrity during respiration by reducing surface tension along the alveolar epithelium. The adsorption, spreading and surface tension-reducing properties of the surfactant phospholipid film are facilitated by specific surfactant-associated proteins, such as SP-B.

Respiratory Distress Syndrome (RDS) is a major cause of mortality among prematurely born infants. It is believed that RDS is caused by a deficiency of lung surfactant. RDS can be effectively treated by administering surfactant proteins and lipids to those individuals suffering from RDS. Purified preparations of surfactant proteins, particularly surfactant protein-B (SP-B) and surfactant protein-C (SP-C), enhance the rate of formation of a phospholipid film at the air-liquid interface, and thus, promote gas exchange in those having RDS. Several lines of evidence indicate that SP-B is a critical component of surfactant: 1) Surfactant replacement preparations containing SP-B as the only protein component were equivalent to natural surfactant and were superior to comparable preparations containing surfactant protein-A SP-A and/or SP-C when tested in vivo (*Am. Rev. Resp. Dis.* 147:669–676, 1993). 2) Addition of SP-B to currently used replacement surfactant preparations (such as Survanta) results in improved surfactant function when tested in vivo (*Pediatr. Res.* 37:271–276, 1995). 3) Mutations in the SP-B gene leading to absence of SP-B in surfactant invariably result in respiratory distress syndrome and death shortly after birth (*N. Engl. J. Med.* 328:406–410, 1993; *Proc. Natl. Acad. Sci. U.S.A.* 92:7794–7798, 1995). 4) Inactivation of SP-B in the airway by interaction with antibodies specific for SP-B leads to respiratory distress syndrome and death (*Exp. Lung Res.* 14:247–260, 1988; *J. Appl. Physiol.* 71:530–536, 1991).

Human SP-B is synthesized by the type II epithelial cell as a 381 amino acid preproprotein (as shown in sequence I.D. No. 1). The 79 residue mature SP-B peptide SEQ ID NO: 2 is extremely hydrophobic and flanked by propeptides of 200 and 102 amino acids at its $NH_2$- and COOH-terminus, respectively SEQ ID NO: 1.

Processing of the precursor protein within the secretory pathway results in cleavage of the signal peptide, followed by proteolytic cleavage of the $NH_2$-terminal and the COOH-terminal propeptides SEQ ID NO: 1 to generate the biophysically active, mature peptide SEQ ID NO: 2. Proteolytic processing of the proprotein occurs in an endosomal/lysosomal compartment, the multi-vesicular body, prior to incorporation of the mature peptide into the lamellar body, which is secreted in response to an appropriate extra cellular stimulus.

The mature SP-B peptide is very hydrophobic, as it consists of approximately 60 percent non-polar amino acids SEQ ID NO: 2. In addition, SP-B is positively charged and has been shown to promote aggregation, disruption and fusion of liposomes containing negatively charged phospholipids. The potential of SP-B to disrupt lipid membranes indicates that the mature peptide must be escorted through the secretory pathway prior to association with surfactant phospholipids.

Pilot-Matias et al, DNA (1989), Vol. 8, No. 2 discloses the isolation, characterization, sequence, and chromosomal localization of the gene encoding human SP-B, as well as the complete nucleotide sequence and deduced amino acid sequence for SP-B. See also Schilling et al, U.S. Pat. No. 4,933,280. The production of mature SP-B through recombinant DNA technology is disclosed in Yao et al, *Biochem Cell Biology* (1990), Vol. 68:559 and Shilling et al, WO88/05820. Various references disclose the expression of surfactant proteins in a variety of systems including the use of fusion proteins in bacterial systems. Schilling et al, WO88/05820; Shilling et al, U.S. Pat. No. 5,430,020.

While the literature discloses the isolation, characterization, sequence, chromosomal localization, and production of SP-B proprotein through recombinant DNA technology, and the isolation and purification of various proteins including SP-B, the literature does not disclose an efficient process for synthesizing mature SP-B recombinantly both in vivo and in vitro, and isolating and purifying the same in a simple, rapid and economically inexpensive process. The prior art discloses methods of recombinantly producing SP-B that require numerous intricate steps of expression, isolation, purification and cleavage which result in very poor yields of mature SP-B. The purification step alone may involve various extracts and solvents which is inefficient, time consuming, and expensive.

BRIEF SUMMARY OF THE INVENTION

The present invention is premised in part on the discovery that mature SP-B can be formed from a preprotein which includes the amino-terminal propeptide but does not include the carboxyl-terminal propeptide SEQ ID NO: 3. This carboxyl propeptide-deficient preprotein having an amino-terminal propeptide SEQ ID NO: 3 can be formed into the mature protein as the mature SP-B can easily be cleaved from the amino-terminal propeptide to form active, mature SP-B SEQ ID NO: 2.

In this invention, mature alveolar surfactant protein B has a propeptide at its amino terminus and has a free carboxyl terminus SEQ ID NO: 3. The propeptide at the amino terminus is comprised of about 200 amino acids SEQ ID NO: 3 while the mature surfactant protein is comprised of 79 amino acids SEQ ID NO: 2.

This mature SP-B protein is formed by forming a fusion protein of SP-B having a propeptide at its amino terminus and a free carboxyl terminus SEQ ID NO: 3, and then cleaving the propeptide at the amino terminus of the fusion protein to thereby liberate the mature SP-B.

More particularly, the process for forming mature SP-B further comprises binding the fusion protein to a solid phase column. The fusion protein is then folded while bound to the solid phase column which, for example, is a nickel chelate-nitrilotriacetic acid Ni-NTA) column. The mature SP-B having a propeptide at its amino terminus SEQ ID NO: 3 is bound to the column by a histidine tag which facilitates separation. The folding of the fusion protein is carried out by washing the protein with a denaturation buffer, and renaturing the fusion protein with a renaturation buffer.

In other subsidiary aspects of the invention, cleaving the propeptide SEQ ID NO: 3 at the amino terminus of the fusion protein is carried out by a cleaving agent. The cleaving agent, for example, is hydroxylamine.

The mature SP-B formed by this process can be administered in vivo. Thus, this form of SP-B can be expressed as a recombinant protein in transgenic animals, mammalian cell lines, insect cells, yeast or bacteria.

The objects and advantages of the present invention may be further appreciated in light of the following detailed description.

DETAILED DESCRIPTION OF THE PREFERRED EMBODIMENT

SP-B is generally expressed as a fusion protein with its own propeptide as shown in sequence ID No. 1. It has been discovered that mature SP-B (as shown in sequence I.D. No. 2) is formed from a COOH-terminally truncated fusion protein such that the approximately 102 amino acid propeptide at the carboxyl terminus are not present, as shown in sequence I.D. No. 3. The 200 amino acid propeptide at the amino terminus SEQ ID NO: 3 are included as they are necessary for the production of mature SP-B. Particularly, the propeptide at the amino terminus i.e., the amino-terminal propeptide, is absolutely required for both folding and transport of the mature peptide in mammalian cells.

The term "amino-terminal preprotein" is used to define the preprotein of SP-B which includes amino acids at the amino terminus but excludes amino acids at the carboxyl terminus SEQ ID NO: 3. This amino-terminal preprotein SEQ ID NO: 3 is formed from a DNA construct. All procedures involving cDNA manipulations may be performed essentially as described in Sambrook et al (1989) *Molecular Cloning: A Laboratory Manual*, Cold Spring Harbor Laboratory Press, Cold Spring Harbor.

Specifically, the sequence encoding the C-terminal propeptide (residues 257–358 SEQ ID NO: 1 ) was deleted from the human SP-B cDNA. An hydroxylamine cleavage cite was introduced at the boundary of the NH$_2$-terminal propeptide and mature peptide, by mutating residues 177–178 (Gln-Phe) SEQ ID NO: 3 to Asn-Gly SEQ ID NO: 5 using standard mutagenesis procedures. An endogenous hydroxylamine cleavage site (residues 111–112) SEQ ID NO: 3 was removed by mutating Asn-Gly to Gln-Gly SEQ ID NO: 5. The resulting SP-B construct SEQ ID NO: 5 was cloned into an expression vector for in vivo or in vitro production of recombinant SP-B.

For expression in vivo, i.e., transgenic animals, the SP-B construct SEQ ID NO: 5 was cloned under control of the SP-C promoter, WAP (whey acid protein) promoter or some other promoter that would restrict expression of SP-B to a specific tissue and thereby facilitate purification of the recombinant protein. Isolation and purification of recombinant SP-B was further aided by insertion of the sequence (CAT)$_6$ or (CAC)$_6$ into the SP-B cDNA construct at a point between the signal peptide and the NH$_2$-terminal propeptide SEQ ID NO: 5. This modification resulted in the secretion of recombinant SP-B in which the first six amino acids were histidine residues, a sequence which binds specifically to Ni-NTA (nickel chelate-nitrilo-triacetic acid). The histidine "tag" and the NH$_2$-terminal propeptide could then be removed by cleavage in vitro with hydroxylamine thereby liberating the mature SP-B peptide.

To produce transgenic animals, the DNA encoding the modified SP-B construct was isolated, purified and injected into fertilized eggs by standard procedures. The advantage of producing SP-B in transgenic animals is that the recombinant protein was folded in the native form and extensive denaturation/renaturation procedures were not required.

Procaryotic systems may be used to express the SP-B fusion sequence. Procaryotic hosts are, of course, the most convenient for cloning procedures. The procaryote most frequently used, and used in the present invention, was *E. coli*. However, other microbial strains may also be used. Transformed microorganisms producing the fusion protein may be grown in any suitable medium containing necessary compounds which fulfill growth requirements of the microorganism.

When performing this procedure in vitro, consecutive histidine residues comprised the only tag that bound to the Ni-NTA column. Other columns with different tags could be used; however, the advantage of the histidine tag/Ni-NTA system is that it permits isolation and purification of tagged proteins under denaturating conditions. Most systems permit purification only under non-denaturing conditions. Recombinant SP-B expressed in *E. coli* was completely insoluble and denatured (as indeed are most eukaryotic proteins expressed in bacteria) and could not be isolated under non-denaturing conditions.

For production in bacteria, the SP-B construct was cloned into the expression vector pProExl (Life Technologies), which included a reiterated CAT sequence at the 5' end of the multi-cloning site resulting in the incorporation of six histidine residues at the amino-terminal propeptide of SP-B, and transformed into DH10B *E. coli*. Recombinant SP-B expression was induced with IPTG for four hours and inclusion bodies subsequently isolated by standard procedures and dissolved in 6 M guanidine/tris-buffered saline. Denatured SP-B was bound to a Ni-NTA agarose column by interaction of the histidine sequence with NTA, and was washed extensively with 6 M urea/tris-buffered saline. Other suitable denaturation buffers include 6 M guanidine hydrochloride in place of 6 M urea and the addition of non-ionic detergents (such as 10 mM octylglusocide) to the guanidine/urea based buffers. Thereafter, the SP-B bound to the agarose was renatured on the column with a renaturation buffer produced by omitting urea from the buffer in the final wash step. It was during this washing and renaturation that the protein properly folded to form the mature SP-B fusion protein.

Soluble recombinant SP-B fusion protein was recovered by eluting the column with 50 mM EDTA/tris-buffered saline. Finally, the propeptide and hexahistidine tags were removed by incubating recombinant SP-B in 2 M hydroxylamine, pH 9.1, for 24 hours at 37° C. The mature peptide was then recovered as a precipitant. Recombinant, mature human SP-B peptide was recovered in both monomer and dimer form. All target protein that bound to the NTA resin in the column was successfully renatured and eluted. It was not necessary to remove the denaturant slowly or gradually as previously suggested in the prior art.

Various methods may be used to cleave the fusion protein thereby liberating the mature SP-B. For purposes of this invention, cleavage with hydroxylamine was required due to the particular cleavage site originally introduced by mutagenesis. Hydroxylamine cleaves specifically between consecutive amino acids asparagine (Asn) and glycine (Gly). Because of the design of the SP-B construct used in this invention, only one such site existed in the recombinant protein, i.e., between the amino-terminal propeptide and the mature peptide. Therefore, both the histidine tag and the amino-terminal propeptide were removed from the mature SP-B by incubating the recombinant protein in 2 M hydroxylamine, pH 9.1, for 24 hours at 37° C. During the cleavage reaction, liberated mature SP-B fell out of solution and was collected by centrifugation. The pellet containing purified recombinant mature SP-B was then readily solubilized in organic solvents, such as chloroform/methanol which facilitated recombination with phospholipids. SP-B/phospholipid mixtures have been shown to comprise excellent replacement surfactants for treatment of respiratory distress syndrome.

Advantageously, only one cleavage site was necessary to cleave the approximately 200 amino acid $NH_2$-terminal propeptide at the amino terminus. If the fusion protein used did not have a free carboxyl terminus at least two cleavage sites would be necessary: one to cleave the $NH_2$-terminal propeptide and one to cleave the COOH-terminal propeptide. This would result in consumption of time and money, and in greater inefficiency.

From the above disclosure of the general principles of the present invention and the preceding detailed description of a preferred embodiment, those skilled in the art will readily comprehend the various modifications to which the present invention is susceptible without departing from the scope of the present invention.

I claim:

1. A synthesized isolated alveolar surfactant protein-B as shown in SEQ ID NO: 7.

2. A process for forming mature surfactant protein-B (SP-B) as shown in SEQ ID NO: 6, comprising:
   (a) forming a fusion protein comprising the amino acid sequence shown in SEQ ID NO: 7; and
   (b) cleaving said fusion protein to thereby liberate said mature SP-B.

3. The process of claim 2 further comprising binding said fusion protein to a solid phase column.

4. The process of claim 3 further comprising folding said fusion protein while bound to said solid phase column.

5. The process of claim 2 wherein said step of cleaving is carried out by a cleaving agent.

6. The process of claim 5 wherein said cleaving agent is hydroxylamine.

7. The process of claim 3 wherein said solid phase column is a nickel chelate-nitrilotriacetic acid (Ni-NTA) column.

8. The process of claim 4 wherein said folding step is carried out by washing said fusion protein with a denaturation buffer, removing the denaturation buffer in a single step, and renaturing said fusion protein with a renaturation buffer.

9. The process of claim 8 wherein said denaturation buffer is comprised of about 6 M urea, about 20 mM Tris, about 500 mM NaCl and about 20 mM imidazole.

10. The process of claim 9 wherein said Tris has a pH of about 7.9.

11. The process of claim 8 wherein said renaturation buffer is Tris-buffered saline.

12. The process of claim 11 wherein said Tris-buffered saline has a pH of about 7.9.

13. The process of claim 4 wherein said mature SP-B protein folded on said solid phase column is soluble in Tris-buffered saline.

14. The process of claim 4 further comprising, after folding but before cleaving, recovering said mature SP-B protein by eluting said mature SP-B protein on said column with an elution buffer.

15. The process of claim 14 wherein said elution buffer is comprised of about 20 mM Tris, about 150 mM NaCl and about 50 mM EDTA.

16. The process of claim 15 wherein said Tris has a pH of about 7.9.

17. The process of claim 2 wherein said cleaving is carried out in vitro.

* * * * *

UNITED STATES PATENT AND TRADEMARK OFFICE
CERTIFICATE OF CORRECTION

| | | |
|---|---|---|
| PATENT NO. | : 6,031,075 | Page 1 of 1 |
| APPLICATION NO. | : 08/596684 | |
| DATED | : February 29, 2000 | |
| INVENTOR(S) | : Timothy E. Weaver | |

It is certified that error appears in the above-identified patent and that said Letters Patent is hereby corrected as shown below:

Column 1, after line 8, before BACKGROUND OF THE INVENTION, please insert:

--STATEMENT REGARDING FEDERALLY SPONSORED RESEARCH

This invention was made with Government support under grant no. R01 HL036055 awarded by the National Institutes of Health. The Government has certain rights in the invention.--

Signed and Sealed this

Twenty-second Day of June, 2010

David J. Kappos
*Director of the United States Patent and Trademark Office*